United States Patent
Zhang et al.

(10) Patent No.: US 9,814,564 B2
(45) Date of Patent: Nov. 14, 2017

(54) RECYCLABLE AND ADJUSTABLE INTERVENTIONAL STENT FOR INTRAVASCULAR CONSTRICTION

(71) Applicant: THE FIRST AFFILIATED HOSPITAL OF NANJING MEDICAL UNIVERSITY, Jiangsu (CN)

(72) Inventors: Shijiang Zhang, Jiangsu (CN); Weidong Gu, Jiangsu (CN)

(73) Assignee: THE FIRST AFFILIATED HOSPITAL OF NANJING MEDICAL UNIVERSITY (CN)

( * ) Notice: Subject to any disclaimer, the term of this patent is extended or adjusted under 35 U.S.C. 154(b) by 141 days.

(21) Appl. No.: 14/354,505

(22) PCT Filed: Oct. 24, 2012

(86) PCT No.: PCT/CN2012/083416
§ 371 (c)(1),
(2) Date: Apr. 25, 2014

(87) PCT Pub. No.: WO2013/060265
PCT Pub. Date: May 2, 2013

(65) Prior Publication Data
US 2014/0303710 A1   Oct. 9, 2014

(30) Foreign Application Priority Data
Oct. 25, 2011   (CN) .......................... 2011 1 0327802

(51) Int. Cl.
*A61F 2/06*   (2013.01)
*A61F 2/07*   (2013.01)
(Continued)

(52) U.S. Cl.
CPC ................. *A61F 2/07* (2013.01); *A61F 2/90* (2013.01); *A61F 2/966* (2013.01);
(Continued)

(58) Field of Classification Search
CPC .... A61F 2/07; A61F 2/90; A61F 2/966; A61F 2/95; A61F 2/962; A61F 2/82; A61F 2/86;
(Continued)

(56) References Cited

U.S. PATENT DOCUMENTS 4,976,733 A * 12/1990 Girardot ............. A61L 27/3687
                                                          427/417
6,254,627 B1 * 7/2001 Freidberg ................. A61F 2/07
                                                          606/195
(Continued)

FOREIGN PATENT DOCUMENTS

CN        2531806       1/2003    ............ A61B 17/00
CN        2706140       6/2005    ............ A61B 17/50
(Continued)

OTHER PUBLICATIONS

International Search Report issued in corresponding PCT Patent Appln. Serial No. PCT/CN2012/083416 dated Jan. 31, 2013, with English translation (8 pgs).

*Primary Examiner* — Melanie Tyson
(74) *Attorney, Agent, or Firm* — Hayes Soloway P.C.

(57) ABSTRACT

A recyclable and adjustable interventional stent for intravascular constriction. The stent main body is divided into three parts and shaped like a waist drum with expansion parts (1, 4) being arranged on the upper and lower parts of the stent main body respectively for supporting and positioning. A variable aperture part (2) is arranged in the middle of the stent main body. The upper expansion part (1) is or is not provided with a coating; the middle variable aperture (Continued)

part (2) and the upper half part of the lower expansion part (4) are covered with a pericardium (3) subjected to anti-calcification treatment; and a metal wire ring (5) is passed through the lowermost edge of the stent. A compound conveying guide pipe is composed of an outer sheath (6) and a core (7). The core (7) is a hollow pipe and a wire hanging groove is arranged on the outer side wall of the tip of the pipe to hang the metal wire ring (5) of the lowermost edge of the stent. A fixing bolt (8) on the outer sheath (6) is used for fixing the relative position between the outer sheath (6) and the core (7). The stent is used to replace conventional pulmonary artery banding as, adhesion not being formed around the heart and major vessels and pulmonary stenosis not being formed, difficulties during radical surgery are not increased.

2 Claims, 2 Drawing Sheets

(51) Int. Cl.
*A61F 2/90* (2013.01)
*A61F 2/966* (2013.01)
A61F 2/95 (2013.01)

(52) U.S. Cl.
CPC .............. *A61F 2002/9522* (2013.01); *A61F 2002/9534* (2013.01); *A61F 2002/9665* (2013.01); *A61F 2210/0061* (2013.01); *A61F 2230/0078* (2013.01); *A61F 2250/001* (2013.01)

(58) Field of Classification Search
CPC ...... A61F 2002/9522; A61F 2002/9528; A61F 2002/9534; A61F 2002/9665; A61F 2210/0061; A61F 2230/0078; A61F 2250/001; A61F 2/89; A61F 2002/828; A61F 2250/0039
USPC ........................................................ 623/1.3
See application file for complete search history.

(56) References Cited

U.S. PATENT DOCUMENTS

| | | | | |
|---|---|---|---|---|
| 6,592,616 | B1 | 7/2003 | Stack et al. | 623/1.17 |
| 6,685,722 | B1* | 2/2004 | Rosenbluth | A61B 17/221 |
| | | | | 606/159 |
| 6,945,994 | B2* | 9/2005 | Austin | A61F 2/91 |
| | | | | 623/1.15 |
| 2002/0143387 | A1* | 10/2002 | Soetikno | A61F 2/95 |
| | | | | 623/1.15 |
| 2003/0233140 | A1* | 12/2003 | Hartley | A61F 2/95 |
| | | | | 623/1.11 |
| 2004/0199243 | A1* | 10/2004 | Yodfat | A61F 2/01 |
| | | | | 623/1.16 |
| 2004/0215324 | A1* | 10/2004 | Vonderwalde | A61F 2/07 |
| | | | | 623/1.15 |
| 2004/0236412 | A1* | 11/2004 | Brar | A61B 17/12045 |
| | | | | 623/1.31 |
| 2006/0155368 | A1 | 7/2006 | Shin et al. | 623/1.31 |
| 2008/0221582 | A1* | 9/2008 | Gia | A61B 17/221 |
| | | | | 606/99 |
| 2009/0069880 | A1* | 3/2009 | Vonderwalde | A61F 2/07 |
| | | | | 623/1.15 |
| 2009/0192601 | A1 | 7/2009 | Rafiee et al. | 623/2.11 |
| 2011/0054589 | A1* | 3/2011 | Bashiri | A61F 2/90 |
| | | | | 623/1.15 |

FOREIGN PATENT DOCUMENTS

| | | | | |
|---|---|---|---|---|
| CN | 1741773 | 3/2006 | ............ | A61F 2/04 |
| CN | 101091675 | 6/2010 | ............ | A61F 2/24 |
| CN | 101152111 | 7/2010 | ............ | A61F 2/90 |
| CN | 201668549 | 12/2010 | ............ | A61F 2/90 |
| CN | 101953724 | 1/2011 | ............ | A61F 2/24 |
| CN | 101961269 | 2/2011 | ............ | A61F 2/24 |
| CN | 102462564 | 5/2012 | ............ | A61F 2/90 |
| CN | 102462565 | 5/2012 | ............ | A61F 2/90 |
| CN | 202409217 | 9/2012 | ............ | A61F 2/90 |
| CN | 202458791 | 10/2012 | ............ | A61F 2/90 |
| WO | WO 01/82831 | 11/2001 | ............ | A61F 2/00 |
| WO | WO 2009/094500 | 7/2009 | ............ | A61F 2/90 |

* cited by examiner

RECYCLABLE AND ADJUSTABLE INTERVENTIONAL STENT FOR INTRAVASCULAR CONSTRICTION

TECHNICAL FIELD

This invention relates to a recyclable and adjustable interventional stent for intravascular constriction.

BACKGROUND ART

Pulmonary artery banding is a palliative operation method commonly used in the treatment of various complex congenital heart diseases, and it is commonly used for children with congenital heart disease. Reduction of pulmonary blood flow and decrease of pulmonary artery pressure are achieved through manually induced stenosis of pulmonary artery. Pulmonary artery banding currently carried out has the following drawbacks: 1. the procedure has to be performed through thoracotomy, with severe trauma and high risk; 2. and thus, general anesthetic and positive pressure respirator must be used, which have great influence on pulmonary artery pressure; 3. during pulmonary artery banding, the extent of constriction is hard to control, so the pulmonary artery pressure upon patient's recovery from anesthesia is usually different from that under anesthesia during surgery, which may result in poor surgical efficacy and high postoperative complication incidence and mortality (13%-31%); 4. the main pulmonary artery may suffer from hypogenesis and relatively severe fibrosis at where banding is fastened, so as to cause stenosis of pulmonary artery artificially, thus when reoperation pulmonary artery angioplasty is required, then the difficulty of operation is increased. Some patients even need a third operation to correct pulmonary artery stenosis due to the development of pulmonary artery fibrosis. Therefore, if this problem could be solved thorough intervention, patients may benefit greatly. In the meantime, it may also be used for other conditions in which decrease of both blood flow and pressure at distal end of a artery is required.

DISCLOSURE OF THE INVENTION

Technical Problems

To overcome the shortages of the currently available pulmonary artery banding, the present invention proposes a recyclable and adjustable interventional stent for intravascular constriction, which has the following advantages: 1. no thoracotomy is needed, so there is only little trauma; 2. no general anesthesia is required, the blood flow and pressure of pulmonary artery measured during the surgery is the same as that after the surgery, so it is easier to achieve satisfactory and stable parameters; 3. the size of the stent could be changed in response to requirements during surgery, so as to improve therapeutic efficacy and decrease postoperative complication incidence and mortality; 4. no adhesion is formed around large cardiac vessels, which provides convenience for further radical operation; 5. no constriction of patient's original pulmonary artery is caused, therefore the difficulty of a subsequent radical operation will not be increased.

SOLUTIONS TO PROBLEMS

Technical Solutions

Technical solutions adopted by the present invention to solve its technical problems comprise two relevant parts: a stent and a composite delivery catheter. 1. The stent: the main body of the stent includes three parts and is dolioform, there is an expanded segment in each of upper end and lower end. The stent is made of memory alloy mesh, and functions for support and positioning. There is a segment with variable diameter in the middle of the main body of the stent, and it is formed by jointing diamond shaped medical stainless steel wire. When the distance between the upper and lower expanded segments of the stent is prolonged, the diamond shaped medical stainless steel wire is unfolded to increase the stent diameter; otherwise, the diamond shaped medical stainless steel wire folds into the lumen of the stent to decrease the stent diameter. The upper expanded segment is covered with or without membrane; the middle segment with variable diameter and the upper half of the lower expanded segment are covered with pericardium treated to prevent calcification; while the lower edge is threaded with a wire ring. The whole stent is compressed into the composite delivery catheter. 2. . The composite delivery catheter is a composite cannula, including two parts: the outer sheath and inner core. The inner core is a hollow tube. Guide wire, contrast media, or other fluids may pass through the hollow inner core. There is a groove for thread hanging on the outer wall at the tip of the tube, which is used to hook the wire at the lower end of the stent; while the outer layer of the inner core is the sheath of the catheter.

During mounting of the stent outside human body, the wire at the lower end of the stent is placed in the thread hanging groove, and covered and fixed by the sheath of the catheter.

After being placed into human body, the whole stent is compressed into the delivery and retrieval catheter. Under the guide of X ray, the guide wire of normal cardiac catheter reaches the main pulmonary artery first. The delivery and retrieval catheter reaches the predetermined position along the guide wire of normal cardiac catheter, then the sheath is retracted to release the stent. The upper expanded segment and the middle segment with variable diameter of the stent stretch automatically, while the lower expanded segment is in a compressed state under the effect of the sheath and inner core. Keep retracting the sheath, the lower expanded segment also stretches. The expanded segments at both ends of the stent function as support and fixing, while the middle narrow segment restricts effective diameter of the pulmonary artery, so as to decrease the pressure of pulmonary artery at the distal end of the narrow segment. The upper expanded segment of the stent is not covered with membrane, so as to prevent the stent from blocking both the left and right openings of the pulmonary artery during moving towards the distal end. Stent with upper expanded segment covered by membrane is used for other vascular conditions.

When adjusting the stent diameter, keep the groove at the front tip of the inner core hooking the wire ring located on the lower edge of the stent, and push the sheath upward to shrink the lower end of the stent, keep the relative location between the sheath and inner core and push both of them upward as a whole, so as to decrease the distance between the upper and lower expanded segments of the stent, and thus to decrease the stent diameter; on the contrary, the stent diameter is increased until reaching the intended diameter, retract the sheath, and the lower expanded segment of the stent is opened and fixed. If all the physiological measurements reach the expected values, push the inner core upwards, to make it detach from the wire ring on the lower edge of the stent. And then withdraw the inner core to finish the stent placement; in case if any parameter is suboptimal, the stent diameter may be adjusted again in accordance with steps described above; if the stent requires retrieval, then keep the groove at the front tip of the inner core hooking the wire ring on the lower edge of the stent, push the sheath upwards to shrink the lower end of the stent, fold the stent inside the sheath, and remove it from human body.

Since placement of stent does not require general anesthesia or thoracotomy, surgical trauma could be avoided. Influence of general anesthetics, use of ventilator and operation on physiological parameters are eliminated; moreover, the stent diameter could be adjusted as needed during the placement of stent, satisfactory and stable parameters could be achieved. Therefore, therapeutic efficacy could be improved and operational complication incidence and mortality could be decreased. With no thoracotomy being carried out, no adhesion is formed around large cardiac vessels. There is no banding ring outside the pulmonary artery, and thus the pulmonary artery stenosis will not be formed, therefore, difficulty during radical surgery is not increased.

BENEFICIAL EFFECTS OF THE INVENTION

Beneficial Effects

Beneficial effects of this invention are:
1. Since no general anesthesia or thoracotomy is performed, there is only minimal trauma, and it is easier to obtain satisfactory and stable parameters, as well as therapeutic efficacy could be improved and postoperative complication incidence and mortality could be decreased.
2. No adhesion will be formed around large cardiac vessels, and the pulmonary artery stenosis will not be formed, therefore, difficulty of the radical surgery is not increased.
3. The stent diameter may be changed based on actual requirements, to suit to different patients or different stages of the same patient.
4. The stent is recyclable, and may be retrieved conveniently as necessary when conditions occur to differ from expectations.

BRIEF DESCRIPTION OF FIGURES

The present invention is further described taking consideration of both figures and embodiments as follows.

In figures, 1. upper expanded segment; 2. middle segment with variable diameter; 3. pericardium covering the stent; 4. lower expanded segment; 5. wire ring on the lower edge of the stent; 6. outer sheath; 7. inner core; 8. mounting bolt.

EMBODIMENTS OF THE INVENTION

Examples of the Invention

Figure 1:
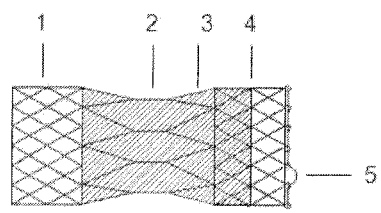
FIG. 1 shows enlarged middle diameter of recyclable and adjustable interventional stent for intravascular constriction of the present invention.
Figure 2:
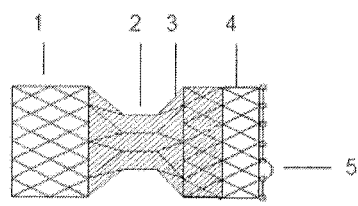
FIG. 2 shows decreased middle diameter of recyclable and adjustable interventional stent for intravascular constriction of the present invention.

In FIG. 1, the stent comprises three parts and is dolioform, the upper expanded segment 1 and the lower expanded segment 4. The stent is made of memory alloy mesh, to function as support and positioning. The middle segment with variable diameter 2 is formed by jointing diamond shaped medical stainless steel wire. The upper expanded segment 1 could be covered with or without membrane, the middle segment with variable diameter 2 and the upper half of the lower expanded segment 4 are covered with pericardium 3 treated to prevent calcification; while the lower edge of the stent is threaded with a wire ring (5). When the distance between the upper expanded segment land lower expanded segment 4 is prolonged, the size of the middle segment with variable diameter 2 is enlarged. It can be seen from FIG. 2 that when the distance between the upper expanded segment 1 and lower expanded segment 4 is decreased, the size of the middle segment with variable diameter 2 is reduced.

Figure 3:
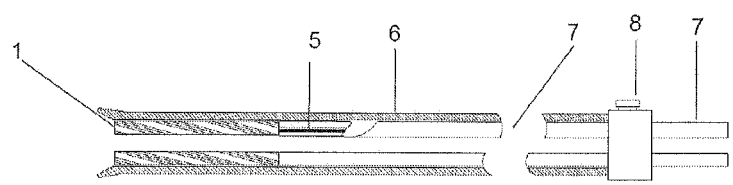
FIG. 3 shows the composite delivery catheter of the present invention.

In FIG. 3, the composite delivery catheter is a composite cannula, the whole stent is compressed into an outer sheath 6, the inner core 7 is located behind the stent, the wire ring 5 on the lower edge of the stent is mounted on the groove of the inner core 7. At the posterior end of the delivery and retrieval catheter, there is a mounting bolt 8 on the outer sheath 6, which is used to maintain relative position between the outer sheath 6 and inner core 7.

Figure 4:
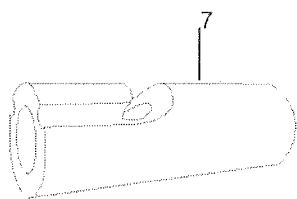
FIG. 4 shows the front tip of inner core of composite delivery catheter of the present invention.

FIG. 4 shows the section of the front tip of composite delivery catheter. It can be seen that the inner core 7 is a hollow tube. There is a groove for thread hanging on the outer wall at the front part of the tube, and it is intended to hook the wire ring 5 on the lower edge of the stent; while the outer layer of the inner core 7 is the outer sheath 6.

Figure 5:
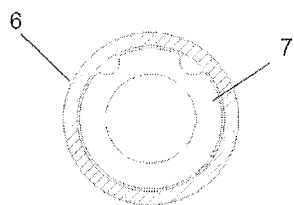
FIG. 5 shows section of front tip of the composite delivery catheter of the present invention.
Figure 6:
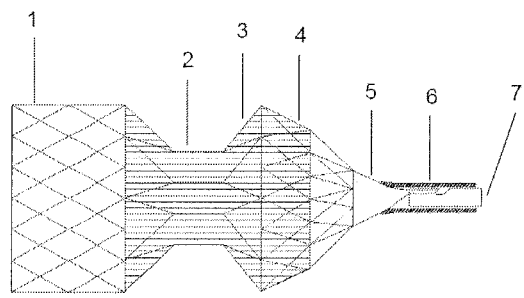
FIG. 6 shows the adjustable diameter of recyclable and adjustable interventional stent for intravascular constriction.

FIG. 5 shows embodiment of adjusting stent diameter and retrieval. Use the groove at the front tip of the inner core 7 to hook the wire ring 5 on the lower edge of the stent, push the sheath 6 upward to shrink the lower end of the stent. And then keep the relative location between inner core 7 and the sheath 6, push both of them upward as a whole, so as to decrease the distance between the upper and lower expanded segments of the stent, and thus to decrease the stent diameter. On the contrary, the stent diameter is to be enlarged. If keep pushing the sheath 7 upward after shrinking the lower end of the stent, the stent could be fold inside the sheath, and be removed from human body.

The invention claimed is:
1. A system for interventional intravascular constriction, comprising a stent and a delivery catheter, wherein, the stent is dolioform in shape and comprises an upper expandable segment and a lower expandable segment, a middle segment having a variable diameter which is different from a diameter of the upper expandable segment, and also is different from a diameter of the lower expandable segment; wherein, the upper expandable segment and the lower expandable segment of the stent are formed of a memory alloy mesh, while the middle segment is formed by jointing diamond-shaped medical stainless steel wire, and the diamond shaped medical stainless steel wire is connected to memory alloy mesh in the upper and lower expandable segments, respectively; wherein the middle segment and an upper portion of the lower expandable segment are covered with pericardium treated to prevent calcification while the upper expandable segment is uncovered; while a lower portion of the stent is threaded with a wire ring adjacent an end of the lower segment, permitting a doctor to adjust or pull the stent from a patient's body; wherein the delivery catheter has a distal end and a proximal end, and comprises an outer sheath and an inner core, wherein the inner core is in the form of a hollow tube, wherein the inner core has a groove formed in an outer wall adjacent a distal end of the tube, for engaging the wire ring on the stent, and a mounting bolt is provided on the proximal end of the delivery catheter.

2. The system according to claim 1, wherein the diameter of the middle segment is adjustable.

\* \* \* \* \*